United States Patent [19]

Harley et al.

[11] Patent Number: 5,252,771
[45] Date of Patent: Oct. 12, 1993

[54] ALUMINUM TRIFLUORIDE CATALYST FOR PRODUCTION OF DIARYL CARBONATES

[75] Inventors: A. Dale Harley; Jose Puga, both of Midland, Mich.

[73] Assignee: The Dow Chemical Company, Midland, Mich.

[21] Appl. No.: 706,426

[22] Filed: May 28, 1991

[51] Int. Cl.$^5$ .............................. C07C 69/96
[52] U.S. Cl. .................................. 558/274
[58] Field of Search ........................ 558/274

[56] References Cited

U.S. PATENT DOCUMENTS

| | | | |
|---|---|---|---|
| 2,362,865 | 7/1941 | Tryon et al. | 558/247 |
| 3,234,263 | 2/1966 | Kurkjy et al. | 558/274 |
| 3,251,873 | 5/1966 | Kurkjy et al. | 558/274 |
| 4,045,464 | 8/1977 | Romano et al. | 558/270 |

OTHER PUBLICATIONS

Advanced Organic Chemistry by Jerry March Third Ed. p. 347.

Primary Examiner—José G. Dees
Assistant Examiner—Joseph M. Conrad

[57] ABSTRACT

A process for the production of a diaryl carbonate useful in the preparation of polycarbonate molding resins comprising contacting an aromatic hydroxy compound and a carbonyl halide or aryl haloformate in the presence of a catalyst comprising aluminum trifluoride.

13 Claims, No Drawings

ALUMINUM TRIFLUORIDE CATALYST FOR PRODUCTION OF DIARYL CARBONATES

The present invention relates to a process and a heterogeneous catalyst for the production of diaryl carbonates. More particularly the present invention relates to a process and a heterogeneous catalyst for the reaction of aromatic hydroxy compounds with carbonyl halides to prepare diaryl carbonates accompanied by elimination of anhydrous hydrogen halide.

Prior art methods for the production of diaryl carbonates have used the interfacial route involving a two phase reaction system, and various homogeneous catalytic systems. The interfacial route involves the neutralization of the aromatic hydroxy compound with caustic and the subsequent reaction of an aqueous solution of the phenate salt of the aromatic hydroxy compound with a carbonyl halide, usually phosgene. In the case where the desired product is diphenyl carbonate, excess caustic to insure the complete neutralization of phenol results in a loss of about 20% of the phosgene. Salt which represents the loss of two chlor/alkali equivalents is produced. As a consequence, the aqueous stream coming from this reaction process requires treatment prior to disposal. Caustic equivalents include the Group 1, 2, 11 and 12 hydroxides, oxides, carbonates and phosphates.

The prior art alternatives to the above described interfacial route to diaryl carbonates includes various homogeneous catalytic processes. As catalysts these processes have used amines and their salts, pentavalent organophosphorous compounds and their salts and organometallic compounds. Anhydrous hydrogen chloride is produced as a side product rather than the waste salt of the interfacial route. This reduces the problem of waste disposal. However, such processes up to now have had the disadvantages of catalyst degradation, and the need to isolate and recycle the catalyst.

U.S. Pat. No. 2,362,865 discloses the use of metal phenates as catalysts in the reaction of phenol and phosgene to form diphenyl carbonate in a process in which the phenol is in the liquid phase. U.S. Pat. No. 3,234,261 relates to the formation of diaryl carbonate from the reaction of various metal oxides with various chloroformates. Related processes are disclosed in French Pat. No. 1,361,228 and U.S. Pat. No. 3,234,263, wherein a tertiary amine base is used as a catalyst.

U.S. Pat. No. 3,251,873 discloses magnesium based catalysts including a magnesium containing zeolites for the preparation of diarylcarbonates. U.S. Pat. No. 4,045,464 teaches the formation of diphenylcarbonates and dialkyl carbonates by contacting phenyl alkyl carbonates with Lewis acid catalysts including aluminum trihalides.

According to the present invention there is provided a process for the production of an aromatic carbonate comprising contacting an aromatic hydroxy compound with a carbonyl halide or aryl haloformate in the presence of a catalytic amount of a catalyst which comprises aluminum trifluoride under conditions sufficient for the formation of aromatic carbonate.

The use of the process and catalyst of the present invention allows for the economical production of diaryl carbonates, which are used in melt polymerization processes to produce polycarbonate resins. These polycarbonate resins are useful as molding resins in the production of shaped articles by the application of heat or other suitable techniques.

The primary object of the present invention is to avoid the disadvantages of the prior art methods of producing diaryl carbonates. These include the water and salt disposal problem associated with the interfacial method, and catalyst degradation and regeneration problems associated with various homogeneous catalytic systems.

The present invention solves the problem of catalyst isolation and recycling by providing an inert insoluble catalyst. Furthermore, the catalysts are highly stable and not subject to volatilization and loss under reaction conditions.

The process of the present invention can be carried out at temperatures much higher than those achievable for homogeneous catalytic processes; high enough, in fact, that in one embodiment some or all reactants and some or all products remain in the gas phase when not in contact with or adsorbed on the catalyst or the catalyst support. These high temperatures have a beneficial effect on the kinetics of the chemical reaction. Suitable operating temperatures are from 25° C. to 450° C., preferably from 150° C. to 400° C., most preferably from 180° C. to 300° C.

The catalyst comprising aluminum trifluoride may be readily prepared by contacting an aluminum oxide such as alumina with hydrogen fluoride at elevated temperatures accompanied by evolution of water. Preferred temperatures for preparing such a catalyst are 250° C. to 700° C., more preferably 450° C. to 600° C. A preferred catalyst has a surface area from 0.1 to 1 $m^2/g$, more preferably 0.3 to 0.75 $m^2/g$. Additionally preferably the catalyst comprises from 50 to 100 percent alpha aluminum trifluoride, more preferably 95 to 100 percent alpha aluminum trifluoride, and most preferably 98 to 100 percent alpha aluminum trifluoride. Other components of the catalyst may include aluminum salts such as oxides, nitrides, halides, etc. and mixtures thereof.

Although the preferred catalysts of the invention are unsupported, the catalyst may also be incorporated onto a support if desired. For example a substrate material may be impregnated with an aluminum salt wherein the anion is an organic anion, such as a carboxylate or a dicarboxylate, for example, oxalate, or a nitrogen containing anion such as nitrate or nitrite. These salts may be converted to the corresponding aluminum oxide by calcining, for example by heating in air at temperatures above about 500° C. Conversion of the alumina coating to $AlF_3$ may then be accomplished as previously disclosed.

Suitable support materials include refractory oxides, ceramics or other inert materials which are porous and stable at high temperatures. Examples include silica, aluminosilicates, carbon, silicon carbide, aluminum nitride, silicalite, titania, zirconia etc.

The porous support material where employed desirably has a surface area from 50 $m^2$ per gram to 500 $m^2$ per gram. The average pore radius of the support material is desirably in the range from 50 Å to 300 Å, while the particle size of the catalyst is desirably from 25 microns to 1.5 cm. The aluminum salt prior to calcining desirably comprises 0.1 to 40 percent by weight of the catalyst, and preferably from 1.0 to 30 percent by weight of the catalyst.

Desirable aromatic hydroxy starting materials to be contacted with the present catalyst are represented by the general formula:

$$Ar(OH)_m$$

where Ar is an aromatic group of up to 24 carbons or a substituted derivative thereof containing up to 5 substituents, and m is 1–3. Suitable substituents include halo or alkyl, alkadiyl, aryloxy, or alkoxy groups of 1 to 12 carbon atoms. Preferred aromatic hydroxy compounds are phenols and bisphenols. Highly preferred aromatic hydroxy starting materials are phenol, bisphenol A (2,2-(4-hydroxyphenyl)propane) and bisphenol F (di(-hydroxyphenyl)methane).

Preferred carbonyl halides are phosgene and bromophosgene. The aryl haloformates may be thought of as the intermediate product resulting from reaction of a carbonyl halide and an aromatic hydroxide. Thus, where present in the reaction mixture, they may be separated from the desired diaryl carbonate and recycled by contacting with the same or another aromatic hydroxide in one embodiment of the present invention.

The process of the present invention is most preferably carried out using phosgene as the carbonyl halide under conditions such that the phosgene is a gas. In a more preferable embodiment both the phosgene and aromatic hydroxide remain in the gas phase when not adsorbed on the catalyst or catalyst support. In one embodiment of the invention the product, diaryl carbonate, may also be a gas, however, preferably it remains a liquid. The temperature ranges that are preferred depend, therefore, upon the liquid to vapor transition temperature of the reactants and the products, the pressure at which the process is carried out, and, as an upper limit, the temperature at which degradation of the product occurs. In a preferred embodiment, where the starting materials are phenol and phosgene, and the product is diphenyl carbonate (DPC), the normal boiling point of phenol is 182° C. and that of the product diphenyl carbonate is 302° C., so the lower limit of the preferred temperature range for the process at 1 atm is 182° C. and the upper limit is 302° C.

In an further embodiment of the invention an inert gas may be employed as a carrier gas, and the reactants and optionally products remain in the gas phase at temperatures below their boiling points. Desirable inert gases for use in the process of this invention are nitrogen, carbon dioxide, and hydrocarbons, such as gaseous toluene. Pressures from about 0.01 atm to about 50 atm may be used, with pressures from about 0.1 atm to about 5 atm being preferred.

A desirable mole ratio of the aromatic hydroxy compound to the carbonyl halide or aryl haloformate is 1:1 to 3:1. Higher ratios of carbonyl halide relative to the aromatic hydroxy compound result in larger amounts of aryl haloformate being formed. From a practical standpoint, it is preferable that the mole ratios be adjusted so that the carbonyl halide is completely consumed. In that way, recycle, removal, or further handling of the carbonyl halide is unnecessary. The aromatic hydroxy compound is more easily recycled. Preferred molar ratios of aromatic hydroxy compound to carbonyl halide are from 1.8:1 to 2.1:1.

The process of the present invention can be carried out in any suitable reactor including a fixed bed reactor, a fluidized bed reactor or a circulating fluidized bed reactor, in which case the catalyst desirably is utilized as a fluidizable powder. Preferred reactors operate under continuous processing conditions. Desirable residence times in such reactors are from 1 to 3000 seconds. Preferred residence times are 1 to 60 seconds. Most preferred are residence times of 1 to 10 seconds. In addition, the rate at which the reactants are contacted with the catalyst in a continuous process is controlled to provide liquid hourly space velocities based on aromatic hydroxy compound preferably in the range from 0.01 to 10 $hr^{-1}$, more preferably from 0.05 to 1 $hr^{-1}$.

Periodic regeneration of the catalyst can improve the conversion rate of starting materials to product. Regeneration is accomplished by treating the catalyst with methanol or water at an elevated temperature in the range of about 400° C. to about 600° C.

The following examples are illustrative of the process of the present invention and are in no way intended to limit the scope of the present invention.

EXAMPLES 1–3

Catalyst Preparation

A catalyst was prepared by reacting gamma $Al_2O_3$ with HF at 500° C. until the evolution of $H_2O$ was complete. Analysis by X-ray diffraction showed the product to be greater than 98 mole percent $AlF_3$ in the alpha crystalline form. The surface area was 0.67 $m^2/gm$. Elemental analysis confirmed the stoichiometric composition.

Polymer Formation

A tubular Hastelloy reactor containing the catalyst was heated to 200° C. and a solution of toluene, phenol, and phenyl chloroformate was introduced. The products were collected in a cooled receiver and analyzed by gas chromatography. The results and experimental conditions are given in Table 1.

EXAMPLES 4–9

Using the same catalyst and reactor as in Example 1, various amounts of a 25 percent molar mixture of phosgene in $N_2$ and a solution of toluene:phenol (1:1 molar ratio) were introduced. The reactor was maintained at 200° C. throughout. The products were collected and analyzed as in Example 1. The experimental parameters and results are given in Table 2.

TABLE 1

| Example | Molar Reactant Ratio (Tol:PhOH:PhOCl) | LHSV[1] ($h^{-1}$) | Diphenyl Carbonate Selectivity[2] | Yield[3] |
|---|---|---|---|---|
| 1 | 1.0:0.5:0.5 | 0.15 | >95 | 42 |
| 2 | 10:1:1 | 0.05 | >95 | 74 |
| 3 | 10:1:1 | 0.12 | >95 | 46 |

[1]Liquid hourly space velocity based on phenylchloroformate
[2]Percent, based on phenol
[3]Percent, based on phenol

TABLE 2

| Ex. | LHSV[1] | DPC[2] yield | PhCOCl[2] yield | Phenol/ $COCl_2$[3] | PhOH (mol/min) | $N_2$+$COCl_2$ (cc/min) | $COCl_2$ (cc/min) |
|---|---|---|---|---|---|---|---|
| 4 | 0.74 | 1.9 | 3.3 | 1.83 | $1.1 \times 10^{-3}$ | 40 | 10 |
| 5 | 0.74 | 3.6 | 5.6 | 0.92 | $1.1 \times 10^{-3}$ | 80 | 20 |

TABLE 2-continued

| Ex. | LHSV[1] | DPC[2] yield | PhCOCl[2] yield | Phenol/ COCl$_2$[3] | PhOH (mol/min) | N$_2$+COCl$_2$ (cc/min) | COCl$_2$ (cc/min) |
|---|---|---|---|---|---|---|---|
| 6 | 0.37 | 5 | 7.1 | 0.92 | $5.5 \times 10^{-4}$ | 40 | 10 |
| 7 | 0.37 | 15.8 | 14 | 1.83 | $5.5 \times 10^{-4}$ | 20 | 5 |
| 8 | 0.183 | 6.8 | 9 | 0.46 | $2.8 \times 10^{-4}$ | 40 | 10 |
| 9 | 0.183 | 9 | 9.4 | 1.83 | $2.8 \times 10^{-4}$ | 20 | 5 |

[1]Liquid hourly space velocity (h$^{-1}$) based on phenol
[2]Percent diphenyl carbonate, based on phenol
[3]Molar ratio The products from both examples were analyzed for aluminum content and the concentration was below the detection limit. This indicates that soluble aluminum phenate type catalysts are not formed during the reaction.

What is claimed is:

1. In a catalyzed process for the production of an aromatic carbonate by contacting an aromatic hydroxy compound with a carbonyl halide or aryl haloformate under conditions sufficient for the formation of an aromatic carbonate, the improvement which comprises utilizing aluminum trifluoride as the catalyst.

2. The process of claim 1 wherein the catalyst has a surface area from 0.1 to 1 m$^2$/g.

3. The process of claim 1 wherein the catalyst is prepared by contacting alumina with hydrogen fluoride at a temperature from 250° to 700° C.

4. The process of claim 1 wherein the catalyst is supported.

5. The process of claim 1 wherein the support is a refractory oxide or ceramic.

6. The process of claim 1 wherein the aromatic hydroxy compound is represented by the general formula:

Ar(OH)$_m$

Ar is an aromatic group of up to 24 carbons or a substituted derivative thereof containing up to 5 substituents, and m is 1–3.

7. The process of claim 6 wherein the substituents are selected from halo and alkyl, alkadiyl, aryloxy, and alkoxy groups of 1-12 carbon atoms.

8. The process of claim 7 wherein the aromatic hydroxy compound is a phenol or bisphenol.

9. The process of claim 1 wherein the carbonyl halide is phosgene.

10. The process of claim 1 wherein the aromatic hydroxy compound is phenol and the aromatic carbonate produced is diphenyl carbonate.

11. The process of claim 1 wherein the temperature is from 25° C. to 450° C.

12. The process of claim 1 wherein the pressure is from 0.01 atm to 50 atm.

13. The process of claim 1 carried out in a reactor with a residence time of from 1 second to 3000 seconds.

* * * * *